United States Patent [19]
Bigg et al.

[11] Patent Number: 5,998,666
[45] Date of Patent: Dec. 7, 1999

[54] PHENOXYETHYLAMINE DERIVATIVES, METHOD OF PREPARATION, APPLICATION AS MEDICINE AND PHARMACEUTICAL COMPOSITIONS CONTAINING SAME

[75] Inventors: Dennis Bigg, Gif-Sur-Yvette; Marie-Odile Galcera, Bondoufle, both of France

[73] Assignee: Societe de Conseils de Recherches Et d'Applications Scientifiques, France

[21] Appl. No.: 09/254,789

[22] PCT Filed: Sep. 26, 1997

[86] PCT No.: PCT/FR97/01690

§ 371 Date: Mar. 11, 1999

§ 102(e) Date: Mar. 11, 1999

[87] PCT Pub. No.: WO98/13337

PCT Pub. Date: Apr. 2, 1998

[30] Foreign Application Priority Data

Sep. 27, 1996 [FR] France ................................. 96/11797

[51] Int. Cl.⁶ .................................................. C07C 233/00
[52] U.S. Cl. ........................... 564/165; 564/167; 564/51; 560/39; 514/620
[58] Field of Search ..................... 564/165, 167, 564/51; 560/39; 514/620

[56] References Cited

U.S. PATENT DOCUMENTS 5,585,492  12/1996  Chandrakumar .

FOREIGN PATENT DOCUMENTS 2531950  2/1984  France .
9505366  2/1995  WIPO .

OTHER PUBLICATIONS

Shutske, "Recent . . . Pharmacology", Expert Opinion on Therapeutic Patents, vol. 4, No. 10, Oct. 1, 1994, pp. 1233–1242.

Glennon, "Concepts . . . Antagonists", Drug Development Research, vol. 26, No. 3, Jan. 1, 1992 pp. 251–274.

Okada et al "Antiemetic . . . Suncus Murinus", The Japanese Journal of Pharamacology, vol. 64, No. 2, Feb. 2, 1994, pp. 109–114.

*Primary Examiner*—Paul J. Killos
*Attorney, Agent, or Firm*—Bierman, Muserlian and Lucas

[57] ABSTRACT

The invention concerns novel phenoxyethylamine derivatives having a high affinity for the $5\text{-HT}_{1A}$ receptor, methods for preparing them, pharmaceutical compositions containing them and their use as medicine and particularly as inhibitors of gastric acid secretion or as antiemetic.

11 Claims, No Drawings

PHENOXYETHYLAMINE DERIVATIVES, METHOD OF PREPARATION, APPLICATION AS MEDICINE AND PHARMACEUTICAL COMPOSITIONS CONTAINING SAME

5-$HT_{1A}$ ligands may be useful for the treatment of anxiety, depression and hypertension (Brain 5-$HT_{1A}$ Receptors: Behavioural and Neurochemical Pharmacology; Editors C. T. Dourish, S. Ahlenius, P. H. Huston; Ellis Horwood LTD, Chischester (1987)).

It has also been shown that 5-$HT_{1A}$ ligands inhibit the secretion of gastric acid (D. C. Evans, J. S. Gidda, *Gastroenterology*, 104, A76 (1993)), exhibit anti-emetic effects (F. Okada, Y. Torii, H. Saito, N, Matsuki, *Jpn. J. Pharmacol.*, 64, 109 (1994)) and act on the motility of the gastrointestinal system (Serotonin and Gastrointestinal Function, Editors T. S. Gaginella, J. J. Galligan; CRC Press, Boca Raton (1995)).

The present invention relates to new derivatives of phenoxyethylamine having a high affinity for the 5-$HT_{1A}$ receptor, processes for their preparation, pharmaceutical compositions containing them, and their use as medicaments, particularly as inhibitors of gastric acid secretion or as anti-emetics.

A subject of the invention is, therefore, products corresponding to general formal I

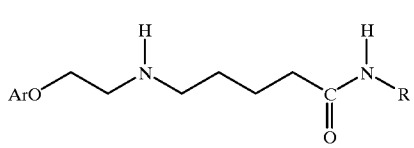

in which
Ar represents a phenyl substituted by one or more substituents;
R represents a hydrocarbon radical containing 1 to 10 carbon atoms chosen from linear or branched alkyl, or cycloalkyl radicals;
and salts of said products.

More particularly, a subject of the invention is the products corresponding to general formula I as defined above, characterised in that the substituent(s) which the phenyl radical represented by Ar may bear are chosen from the lower alkoxy, —C(O)$NR_1R_2$, —NHC(O)$R_3$, —NHC(O) $NR_4R_5$, —NHC(O)$OR_6$ radicals, in which $R_1$, $R_2$, $R_3$, $R_4$ and $R_5$ represent, independently, a hydrogen atom or a lower alkyl, and $R_6$ represents a lower alkyl.

In the definitions given above, the expression lower alkyl represents preferably a linear or branched alkyl radical having 1 to 6 carbon atoms, such as the methyl, ethyl, propyl, isopropyl, butyl, isobtuyl, sec-butyl, tert-butyl, isopentyl, neopentyl and hexyl radicals.

The cycloalkyl radicals may be chosen from saturated monocyclic radicals having 3 to 7 carbon atoms such as cyclopropyl, cyclobutyl, cyclopentyl, cyclohexyl or cycloheptyl radicals.

The lower alkoxy radicals may correspond to the lower alkyl radicals indicated above. Methoxy, ethoxy or isopropyloxy radicals are preferred.

The products corresponding to formula I may form addition salts with acids, particularly pharmacologically acceptable acids.

Examples of salts are given below in the experimental part.

A subject of the invention is in particular compounds corresponding to general formula I as described above, characterised in that Ar represents a phenyl radical substituted by a substituent chosen from the methoxy, —C(O) NHMe, —NHC(O)Me, —NHCONH$_2$, —NHCONHMe, NHC(O))Me radicals, and in that R represents the tert-butyl, neopentyl, cyclopentyl, cyclohexyl or cycloheptyl radical.

The substituents of the phenyl radical which Ar may represent are preferably situated in position 2 or 3.

More particularly, a subject of the invention is the products described below in the examples, particularly the products corresponding to the following formulae:

N-tert-butyl-5-[{2-(2-methoxyphenoxy)ethyl}amino] pentanamide;
N-cyclohexyl-5-[{2-(2-methoxyphenoxy)ethyl}amino] pentanamide;
N-neopentyl-5-[{2-(2-methoxyphenoxyl)ethyl}amino] pentanamide;
N-cyclopentyl-5-[{2-(2-methoxyphenoxy)ethyl}amino] pentanamide;
N-cycloheptyl-5-[{2-(2-methoxyphenoxy)ethyl}amino] pentanamide;
N-cyclohexyl-5-[{2-(2-(methylaminocarbonyl)phenoxy) ethyl}amino]pentanamide;
N-neopentyl-5-[{2-(2-(methylaminocarbonyl)phenoxy) ethyl}-amino]pentanamide;
N-neopentyl-5-[{2-(2-(aminocarbonylamino)phenoxy) ethyl}-amino]pentanamide;
N-neopentyl-5-[{2-(3-(aminocarbonylamino)phenoxy) ethyl}-amino]pentanamide;
N-cycloheptyl-5-[{(2-(3-aminocarbonylamino)phenoxy) ethyl}amino]pentanamide;
N-cyclohexyl-5-[{2-(3-(methylcarbonylamino)phenoxy) ethyl}amino]pentanamide;
N-neopentyl-5-[{2-(3-(methylcarbonylamino)phenoxy) ethyl}-amino]pentanamide;
N-neopentyl-5-[{2-(3-(methoxycarbonylamino)phenoxy) ethyl}amino]pentanamide;
N-neopentyl-5-[{2-(3-(methylaminocarbonyl)phenoxy) ethyl}-amino]butanamide; and the salts of said compounds with inorganic or organic acids.

The invention also provides a process for the preparation of products corresponding to general formula I as defined above, characterised in that
A) either a product corresponding to formula II

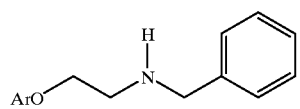

in which Ar has the meaning given above, is allowed to react with a product corresponding to formula III

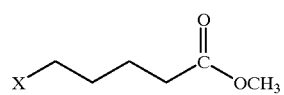

in which X represents a halogen or a pseudo halogen, in order to obtain a product corresponding to formula IV

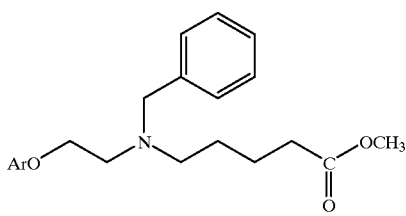

IV which product corresponding to formula IV is treated with an amino corresponding to the formula $RNH_2$ in which R has the meaning given above, in order to obtain a product corresponding to formula V.

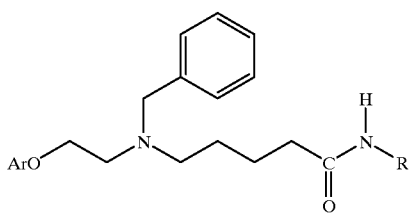

V which product corresponding to formula V is converted to a product corresponding to formula I by cleavage of the benzyl function, and which product corresponding to formula I may be converted to acid salts by the action of the corresponding acid.

B) or a product corresponding to formula VI

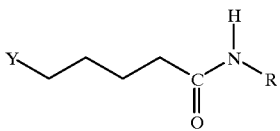

VI in which Y represents a halogen or pseudo halogen radical and R has the meaning given above is allowed to react with N-benzylethanolamine corresponding to the formula

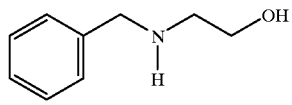

in order to obtain a product corresponding to formula VII

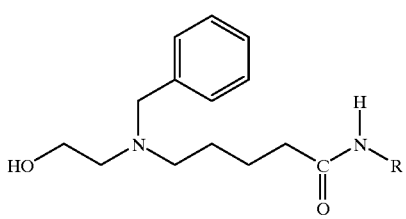

VII which is converted to a product corresponding to formula VIII

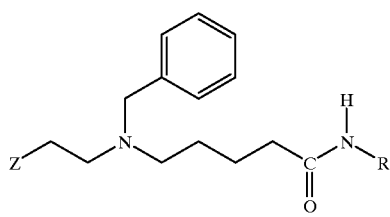

VIII in which Z represents a halogen or pseudo halogen radical, which product corresponding to formula VIII is allowable to react with a compound corresponding to the general formula ArOH in which Ar has the meaning given above, in order to obtain a product corresponding to formula V as defined above, which product corresponding to formula V is converted to a product corresponding to formula I by cleavage of the benzyl function, and which product corresponding to formula I may be converted to acid salts by the action of the corresponding acid.

In the syntheses as presented above, X, Y and Z represent, independently, a leaving group such as chloro, bromo, iodo, emthanesulfonyloxy, benzenesulfonyl oxy or p-toluenesulfonyloxy, in other words, a halogen or pseudo halogen group.

The reaction of a compound corresponding to general formula II with a compound corresponding to general formula III in order to obtain a compound corresponding to general formula IV may be carried out easily by heating in a polar solvent, for example, acetonitrile or dimethylformamide, in the presence of an inorganic base such as potassium carbonate or sodium carbonate and optionally a catalyst such as potassium iodide.

The esters corresponding to general formula IV thus obtained may be converted to amides corrresponding to general formula V by reaction with the corresponding amine by heating said two compounds, with reflux of the amine, without solvent, preferably under a nitrogen atmosphere or in aromatic hydrocarbon in the presence of molecular sieve.

Depending on the substituents present on the phenyl radical which Ar represents, the amides V may also be obtained after hydrolysis of the ester function and peptide coupling with the amines corresponding to general formula $RNH_2$. The amides corresponding to general formula V may also be obtained by reaction of sodium diethyldiaminoaluminates or of an amide complex of lithium and aluminium, prepared from amines corresponding to general formula $RNH_2$ according to known methods such as those described, for example, in Synlett, 10, 827–8 (1994) or in J. Org. Chem., 57(22), 5831–4 (1992), with esters corresponding to general formula IV.

Compounds corresponding to general formula VII may be prepared by heating a compound corresponding to general formula VI with N-benzylethanolamine in a polar solvent such as an alcohol in the presence of an acid acceptor such as a tertiary amine or an inorganic base such as sodium carbonate or potassium carbonate, Alternatively, compounds corresponding to general formula VII may be prepared easily by simply heating a compound corresponding to general formula VI with an excess of N-benzylethanolamine in the absence of a solvent preferably under a nitrogen atmosphere and at a temperature between 60° C. and 90° C.

The compounds corresponding to general formula VII thus obtained may be converted, for example, to chlorides corresponding to general formula VIII (Z=Cl) by reaction with methanesulfonyl chloride in an inert solvent such as dichloromethane and in the presence of an organic base such as triethylamine or diisopropylethylamine.

Compounds corresponding to general formula V may be prepared from compounds corresponding to general formula VIII by reacting these latter with a phenoxide anion produced from the appropriate compound corresponding to formula ArOH, using a base such as sodium hydroxide, potassium hydroxide, or sodium hydride. The reaction is carried out in an aprotic solvent and, preferably, in a dipolar aprotic solvent such as, for example, dimethylformamide.

The compounds corresponding to general formula I are obtained by deprotecting the compounds corresponding to general formula V according to general methods known to the person skilled in the art for debenzylation such as, for example, catalytic hydrogenation or the reaction with a chloroformate such as vinylchloroformate or -chloroethylchloroformate followed by hydrolysis or methanolysis. Other methods of debenzylation as described in Protective Groups in Organic Synthesis (T. W. Green, P. G. M. Wuts; 2nd Ed., J. Wiley and sons Inc., p. 364–6 (1991)) may also be used provided they are compatible with the substituents on the aromatic nucleus of the compounds corresponding to general formula V.

Optional conversion to salts of the products corresponding to formula I is also carried out according to the usually methods indicted below in the experimental part.

The compounds of the present invention have advantageous pharmacological properties. It was thus discovered that the compounds of the present invention have a high affinity for the 5 $HT_{1A}$ receptor. The compounds of the present invention may thus be used in various therapeutic applications.

The compounds may inhibit the secretion of gastric acid. They may inhibit vomiting induced, for example, by cisplatin. Thus, the compounds of the invention may be used as anti-emetics or for the treatment of diseases in which it is necessary or desirable to reduce the secretion of gastric acid by, for example, gastric or duodenal ulcers, gastritis, gastro-oesophageal reflux, gastric dyspepsia, Zolling-Ellison syndrome, nausea.

The compounds of the invention may also exhibit activity with respect to gastric emptying and intestinal motility. They may thus be used to combat constipation, post-operative atonia, gastroparesis.

They may also be used for the treatment of certain diseases of the nervous system such as anxiety, depression, sleep disorders such as insomnia, dependence on certain drugs, Alzheimer's disease, dizziness, eating disorders such as anorexia. The compounds of the invention may also be used to treat diseases of the cardiovascular system, particularly hypertension.

An illustration of the pharmacological properties of the compounds of the invention will be formed below in the experimental part.

Said properties render the products corresponding to formula I suitable for pharmaceutical use. The present application also provides, as medicaments, the products corresponding to formula I as defined above, and the addition salts with pharmaceutically acceptable inorganic or organic acids of said products corresponding to formula I, and pharmaceutical compositions containing, as active principle, at least one of the medicaments as defined above.

The invention thus relates to pharmaceutical compositions containing a compound of the invention or an addition salt of a pharmaceutically acceptable acid of the latter in combination with a pharmaceutically acceptable carrier. The pharmaceutical composition may be in the form of a solid, for example, powders, granules, tablets, capsules or suppositories. Suitable solid carriers may be, for example, calcium phosphate, magnesium stearate, talc, sugars, lactose, dextrin, starch, gelatin, cellulose, methylcellulose, sodium carboxymethylcellulose, polyvinylpyrrolidone and wax.

The pharmaceutical compositions containing a compound of the invention may also be in the liquid form, for example, solutions, emulsions, suspensions or syrups. Suitable liquid carriers may be, for example, water, organic solvents such as glycerol or glycols and mixtures thereof in various proportions in water, added to pharmaceutically acceptable oils or fats. The sterile liquid compositions may be used for intramuscular, intraperitoneal or subcutaneous injections, and the sterile compositions may also be administered intravenously.

The invention also provides the use of the products corresponding to formula I as defined above for the preparation of anti-emetic medicaments, medicaments intended to reduce gastric secretion, medicaments intended to accelerate gastric emptying, medicaments intended to modify intestinal transit, medicaments intended to treat anxiety, depression, sleep disorders and medicaments intended to treat cardio-vascular diseases.

The invention also provides, as new industrial products, and particularly as new industrial products intended for the preparation of products corresponding to formula I, products corresponding to formulae IV, V, VII and VIII as described above.

The starting products of the invention, particularly the products corresponding to formulae II, III and VI, are known products or which may be prepared from known products. The following references may be cited: N-benzylethanolamine is a product sold, for example, by ACROS. The products corresponding to formula II may be prepared by conventional methods from the corresponding phenoxyethylamines, for example, by way of benzamide followed by reduction by lithium aluminium hydride or an equivalent method. Alternatively, a reducing amination may be used according to the usual methods.

The phenoxyethylamines may be prepared according to the usual methods, for example, by reaction of a phenol with chloroacetonitrile in a basic medium, a reaction followed by reduction of the nitrile by lithium aluminium hydride according to the method described in Chim. Ther. 8(3), 259–270 (1973).

The products corresponding to formula III are commercial products or may be produced by methods known to the person skilled in the art. Thus, the product corresponding to formula III, in which X represents a chlorine atom, is sold by ACROS.

The products corresponding to formula VI may be prepared according to known methods from pentanoic acid, substitute din the 5 position by a halogen or a pseudo halogen, or activated derivatives such as the acid chloride or the activated ester, with which are reacted the amines corresponding to general formula $RNH_2$.

The phenolic derivatives corresponding to the general formula ArOH are commercial products or may be produced by methods known to the person skilled in the art.

The examples below are presented in order to illustrate the procedures above and should not in any case be regarded as limiting the scope of the invention.

EXPERIMENTAL PART

EXAMPLE 1

N-cyclohexyl-5-[{2-(2-methoxyphenoxy)ethyl}amino] pentanamide (I, Ar=2-methoxyphenyl, R=cyclohexyl: compound no. 2, Table 1)

First step

Methyl-5-[benzyl{2-(2-methoxyphenoxy)ethyl}amino] pentanoate (IV, Ar-=2-methoxyphenyl)

Potassium carbonate (28.6 g, 0.21 mole) and potassium iodide (0.2 g, 1.2 mmole) are added to a solution of N-benzyl[2-(2-methoxyphenoxy)ethylamine hydrochloride (26.4 g, 0.09 mole) in dimethylformamide (100 mol). The reaction mixture is agitated for 10 minutes at 20° C., then a solution of methyl-5-chloropentanoate (15 g, 14.3 ml, 0.1 mole) in dimethylformamide (30 ml) is added dropwise. The mixture is agitated and heated to 60° C. for 24 hours, then filtered and the solvent is evaporated under reduced pressure. The residue is taken up in dichloromethane (100 ml), washed with water (3×50 ml) and dried over magnesium sulfate, Filtration and evaporation of the solvent lead to an oil which is purified by flash chromatography over silica gel in a mixture of ethyl acetate/heptane (1/1). 30 g (91%) of the desired compound are obtained.

NMR-$^1$H (CDCl$_2$,:1.55–1.80 (m, 4H), 2.30 (t, 2H, J=8 Hz), 2.60 (t, 2H, J=6 Hz), 2.92 (t, 2H, J=6 Hz), 3.66 (s, 3H), 3.69 (s, 3H), 4.07 (t, 2H, J=6 Hz), 6.80–6.95 (m, 4H), 7.20–7.40 (m, 5H).

Second Step

N-cyclohexyl-5-[benzyl{2-(2-methoxyphenoxy) ethyl}amino]pentanamide (V, Ar=2-methoxyphenyl; R=cyclohexyl)

A solution of sodium diethyldihydroaluminate (4.44 ml, 8.9 mmole) in a concentration of 2 moles per liter in toluene, is added to a solution of cyclohexylamine (1.76 g, 2.03 ml, 18 mmole) in anhydrous toluene (60 ml). The reaction mixture is heated to 110° C. for 1 hour, then a solution of methyl-5-[benzyl{2-(2-methoxyphenoxy)ethyl}amino] pentanoate (6 g, 16 mmole) in toluene (25 ml) is added dropwise. The mixture is heated under reflux for 3 hours and left for 18 hours at 20° C., then neutralised with a 10% solution of acetic acid. The organic phase is extracted then washed successively with a saturated solution of sodium hydrogen carbonate then with water. After drying over magnesium sulfate and evaporation of the solvents under reduced pressure, the product is purified by flash chromatography over silica gel in a mixture of ethyl acetate/heptane (2/1). 3.3 g (47%) of the desired product are obtained in the form of an oil.

NMR-$^1$H (CDCl$_3$,:1.00–1.80 (m, 14H), 2.10 (t, 2H, J=6.6 Hz), 2.60 (t, 2H, J=7.6 Hz), 290 (t, 2H, J=6 Hz), 3.67 (s, 2H), 3.85 (s, 3H), 4.08 (t, 2H, J=6 Hz), 6.80–6.90 (m, 4H), 7.25–7.40 (m, 5H).

Third Step

N-cyclohexyl-5-[{2-(2-methoxyphenoxy)ethyl}amino] pentanamide (I, Ar=2-methoxyphenyl, R=cyclohexyl)

A catalyst composed of palladium on 10% moist carbon (1.5 g) is added to a solution of N-cyclohexyl-5-[benzyl{2-(2-methoxyphenoxy)ethyl}amino]pentan-amide (3 g, 6.8 mmole) in glacial acetic acid (30 ml) and the mixture is hydrogenated for 2 hours at 20° C. The catalyst is removed by filtration and the solvent is evaporated under reduced pressure. The residue obtained in the form of a salt of acetic acid is taken up in dichloromethane (50 ml) and the base is liberated by treatment with a saturated solution of sodium hydrogen carbonate. The organic phase is collected, washed with water, dried over magnesium sulfate and the solvent is evaporated under reduced pressure. The expected product is obtained in the form of a white powder after crystallisation in diethylether (0.95 g, 40%).

The treatment of a solution of this free base (0.72 g) in ethanol under hot conditions with a hot ethanolic solution of fumaric acid (0.24 g) gives 0.8 g of compound no. 2 in the form of white crystals, m.p.=141.5–144° C.

NMR-$^1$H (DMSO),:1.05–1.30 (m, 5H), 1.50–1.70 (m, 9H), 2.07 (t, 2H, J=6.6 Hz), 2.94 (t, 2H, J=6.9 Hz), 3.23 (t, 2H, J=5.3 Hz), 3.50 (m, 1H), 3.77 (s, 3H), 4.21 (t, 2H, J=5.3 Hz), 6.50 (s, 2H), 6.89–7.03 (m, 4H), 7.71 (d, 1H, J=7.8 Hz).

NMR-$^{13}$C (DMSO),:22.81, 24.88, 25.31, 25.72, 32.78, 32.91, 35.07, 46.06, 47.30, 47.53, 55.53, 55.78, 65.52, 112.50, 114.74, 120.83, 121.00, 122.26, 135.02, 147.47, 149.58, 168.04, 170.88.

IR (Nujol), cm$^{-1}$:3278 (N-H), 1714 (C=O), 1635 (C=O), 1548 (C-N), 1577 (C=C), 741 (aromatic C-H).

EXAMPLE 2

N-cyclcoheptyl-5-[{2-(3-(aminocarbonylamino) phenoxy)ethyl}amino]pentanamide (I, Ar=3-(aminocarbonylamino)phenyl, R=cycloheptyl: compound No. 10, Table 1)

First step

N-cyclohepty-5-[benzyl(2-hydroxyethyl)amino] pentanamide (VII, R=cycloheptyl)

N-cycloheptyl-5-bromopentanamide (4.15 g, 15 mmole) in solution in dimethylformamide (20 ml) is added dropwise to a hot solution (60° C.) of N-benzylethanolamine (2.27 g, 2.13 ml, 15 mmole) in dimethylformamide (25 ml) in the presence of potassium carbonate (4.15 g, 3 mmole). The reaction mixture is agitated for 2 hours at 60° C. then the solvent is evaporated under reduced pressure. The residue is taken up in dichloromethane (50 ml) and washed with water (3×30 ml). The organic phase is collected, dried over magnesium sulfate; the solvent is evaporated under reduced pressure. The product obtained is purified by flash chromatography over silica gel in a mixture of dichloromethane/methanol (90/10) to give 3.04 g (50%) of the expected compound in the form of an oil.

Second step

N-cycloheptyl-5-[benzyl(2-chloroethyl)amino] pentanamide (VIII, Z=Cl, R=cycloheptyl)

Methanesulfonyl chloride (0.78 g, 0.52 ml, 6.6 mmole) is added dropwise with stirring to a cooled solution of N-cycloheptyl-5-[benzyl(2-hydroxyethyl)amino] pentanamide (2.14 g, 6 mmole) in dichloromethane (20 ml) in the presence of triethylamine (0.69 g, 0.94 ml, 6.6 mmole). Agitation is maintained for 18 hours at 20° C. The reaction mixture is filtered with iced water (25 ml) then dried over magnesium sulfate. Filtration and evaporation of the solvent under reduced pressure give 2.2 g (98%) of the desired compound in the form of an oil.

NMR-$^1$H (CDCl$_3$),:1.35–2.00 (m, 16H), 2.54 (t, 2H, J=6 Hz), 2.83 (t, 2H, J=5 Hz), 2.95 (t, 2H, 5 Hz), 3.53 (t, 2H, J=6 Hz), 3.67 (s, 2H), 4.20 (m, 1H), 4.45 (m, 1H), 7.31 (s, 5H).

Third step

N-cycloheptyl-5-[benzyl{2-(3-(aminocarbonylamino) phenoxy)ethyl}amino]pentanamide (V, Ar=3-(aminocarbonyl amino)phenyl, R=cycloheptyl)

Potassium carbonate (0.92 g, 6.6 mmole) is added to a solution of 3-hydroxyphenylurea (1 g, 6.6 mmole) in dimethylformamide (20 ml) and said mixture is stirred for 10 minutes at 20° C. A solution of N-cycloheptyl-5-[benzyl-(2-chloroethyl)amino]pentanamide (2.21 g, 6 mmole) in dimethylformamide (20 ml) is then added dropwise, the mixture being kept under agitation for 4 hours at 80° C. The solvent is evaporated under reduced pressure, then the residue is taken up in dichloromethane (50 ml) and washed with water. The organic phase is collected and dried then, after evaporation of the solvent, the desired compound is obtained in the form of an oil. It is purified by flash chromatography over silica gel in a mixture of dichloromethane/methanol (95/5) to give 1.75 g (60%) of pure compound. NMR-$^1$H (CDCl$_3$),;1.30–1.90 (m, 16H), 2.12 (t, 2H, J=6 Hz), 2.53 (t, 2H, J=6 Hz), 2.80 (t, 2H, J=6 Hz), 3.63 (s, 2H), 3.95 (m, 1H), 4.07 (t, 2H, J=6 Hz), 4.93 (s, 1H), 5.55 (m, 1H), 6.68 (m, 2H), 7.19 –7.30 (m, 9H).

Fourth step

N-cyclohepty-5-[{2-(3-(aminocarbonylamino)phenoxy)ethyl}amino]pentanamide

A catalyst composed of palladium of 10% moist carbon (0.3 g) is added to a solution of N-cycloheptyl-5-[benzyl{2-(3-aminocarbonyl amino)phenoxy)ethyl}amino]pentanamide (0.6 g, 1.2 mmole) in methanol (20 ml) and the mixture is hydrogenated for 24 hours at 20° C. The catalyst is then filtered and replaced by the same quantity. Hydrogenation is continued for another 24 hours. The catalyst is removed by filtration and the solvent is evaporated under reduced pressure. The desired product is obtained after purification by flash chromatography over silica gel in a mixture of dichloromethane/methanol/ammonia solution (90/10/1) (0.25 g, 51%). The treatment of a solution of this free base (0.11 G) in ethanol under hot conditions with a hot ethanolic solution of fumaric acid (33 mg) gives 0.14 g of compound no. 10 in the form of white crystals, m.p.=80–85° C.

NMR-$^1$H (DMSO),:1.34–1.73 (m, 16H), 2.05 (t, 2H, J=6.4 Hz), 2.84 (t, 2H, J=6.5 Hz), 3.18 (t, 2H, J=4.9 Hz), 3.70 (m, 1H), 4.11 (t, 2H, J =5.0 Hz), 5.97 (s, 2H), 6.48 (s, 2H), 6.87 (d, 1H, J=8.0 Hz), 7.11 (t, 1H, J=8.1 Hz), 7.28 (m, 1H), 7.73 (d, 1H, J=7.7 Hz), 8.84 (s, 1H).

IR (KBr), cm$^{-1}$:3350 (N-H), 1700 (C=)), 1677 (urea), 1638 (C=O), 1590 (C=C), 1550 (C-N)

The processes described above give a composition of the invention in the form of a free base or an addition salt with an acid. If the compound of the invention is obtained in the form of an addition salt with an acid, the free base may be obtained by converting a solution of the addition salt to a base with a base. Conversely, if the product of the process is a free base, the addition salt with an acid, particularly an addition salt with a pharmaceutically acceptable acid, may be obtained by dissolving the free base in an appropriate organic solvent and treating the solution with an acid, according to conventional procedures for the preparation of addition salts with an acid from free bases.

Examples of addition salts with an acid are those derived from inorganic acids such as sulfuric, hydrochloric, hydrobromic or phosphoric acid, or organic acids such as tartaric, fumaric, maleic, citric, caprylic, benzoic, methanesulfonic, p-toluenesulfonic, benzenesulfonic, succinic or acetic acid.

As regards the compounds of the invention containing an asymmetrical centre, the racemic mixtures and the individual optically active isomers are also considered to be part of the scope of the invention.

Table 1 below shows the main compounds prepared according to the above procedures and which illustrate the invention without limiting its scope. Compounds nos. 2 and 10 correspond respectively to the products of example 1 and 2 described above. The other products were prepared using the same process.

TABLE 1

| Compound No. | Ar | R | Salt | m.p. (° C.) |
|---|---|---|---|---|
| 1 | 2-MeO.C$_6$H$_4$ | tert-butyl | fumarate | 146–147 |
| 2 | 2-MeO.C$_6$H$_4$ | cyclohexyl | fumarate | 141.5–144 |
| 3 | 2-MeO.C$_6$H$_4$ | neopentyl | fumarate | 128.5–131 |
| 4 | 2-MeO.C$_6$H$_4$ | cyclopentyl | fumarate | 128–129.5 |
| 5 | 2-MeO.C$_6$H$_4$ | cycloheptyl | fumarate | 131–134 |
| 6 | 2-MeNHC(O)C$_6$H$_4$ | cyclohexyl | fumarate | 126–129.5 |
| 7 | 2-MeNHC(O).C$_6$H$_4$ | neopentyl | fumarate | 143.5–145 |
| 8 | 2-H2NC(O)NH.C$_6$H$_4$ | neopentyl | fumarate | 153–154.5 |
| 9 | 3-H2NC(O)NH.C$_6$H$_4$ | neopentyl | fumarate | 150.5–152.5 |
| 10 | 3-H2NC(O)NH.C$_6$H$_4$ | cycloheptyl | fumarate | 81–85 |
| 11 | 3-MeC(O)NH.C$_6$H$_4$ | cyclohexyl | hemi-fumarate | 176–177 |
| 12 | 3-MeC(O)NH.C$_6$H$_4$ | neopentyl | 0.75-fumarate | 165.5–168.5 |
| 13 | 3-MeOC(O)NH.C$_6$H$_4$ | neopentyl | fumarate | 124.5–125 |
| 14 | 3-MeNHC(O)NH.C$_6$H$_4$ | neopentyl | fumarate | 154.5–155.5 |

| Compound | Ar | R |
|---|---|---|
| A | 3-MeO.C$_6$H$_4$ | ethyl |
| B | 3-EtO.C$_6$H$_4$ | neopentyl |
| C | 3-MeO.C$_6$H$_4$ | cyclohexyl |
| D | 2-NH2C(O).C$_6$H$_4$ | methyl |
| E | 2-NH2C(O).C$_6$H$_4$ | cyclopentyl |
| F | 2-MeNHC(O).C$_6$H$_4$ | cyclopentyl |
| G | 3-EtNHC(O).C$_6$H$_4$ | methyl |
| H | 2-(Me)$_2$NC(O).C$_6$H$_4$ | cycloheptyl |
| I | 3-EtNHC(O).C$_6$H$_4$ | cycloheptyl |
| J | 2-MeC(O)NH.C$_6$H$_4$ | neopentyl |
| K | 3-MeC(O)NH.C$_6$H$_4$ | cyclopentyl |
| L | 3-EtC(O)NH.C$_6$H$_4$ | tert-butyl |
| M | 3-HC(O)NH.C$_6$H$_4$ | cyclopentyl |
| N | 2-H$_2$NC(O)NH.C$_6$H$_4$ | cyclohexyl |
| O | 2-MeNHC(O)NH.C$_6$H$_4$ | neopentyl |
| P | 2-(Me)$_2$NC(O)NH.C$_6$H$_4$ | cycloheptyl |
| Q | 3-MeNHC(O)NH.C$_6$H$_4$ | n-propyl |
| R | 3-EtNHC(O)NH.C$_6$H$_4$ | methyl |
| S | 2-MeOC(O)NH.C$_6$H$_4$ | neopentyl |
| T | 2-EtOC(O)NH.C$_6$H$_4$ | cycloheptyl |
| U | 3-C$_3$H$_7$OC(O)NH.C$_6$H$_4$ | tert-butyl |

Pharmacological Study of the Products of the Invention

Affinity of the compounds of the invention for the 5-HT$_{1A}$ receptor

The affinity of the compounds for serotonergic 5-HT1A receptors is determined by measuring the inhibition of [3H]8-hydroxy-2-(di-n-propylaminotetralin ([3H]8-OH-DPAT) bound to the cerebral cortex of the rat, according to the method of Peroutka and his coworkers [(*J. Neurochem.,* 47, 529 (1986)].

Cerebral cortices of male Sprague Dawley rats are homogenised in Tris-HCl 50 mM, pH=7.4 and centrifuged at 40,000 g for 10 min at 4° C. Pellets are resuspended in the same buffer and incubated for 10 min at 37° C., and the homogenised products are centrifuged again at 40,000 g for 10 min at 4° C.

Competitive inhibition tests of [3H]8-OH-DPAT binding are carried out three times with unlabelled competitors, with concentrations between 100 pM and 100 μM. Cerebral cortex membranes of rats (10 mg wet weight/ml) are incubated with [3H]8-OH-DPAT (1 nM) for 30 min at 25° C. in Tris-HCl 50 mM, pH=7.4 containing 4 mM of CaCl$_2$, 10M of paragyline and 0.1% of ascorbic acid.

The bound [3H]8-OH-DPAT is separated from free [3H]8-OH-DPAT by immediate filtration by means of Whatman GF/B glass fibre filters using a Brandel cell recovery device. The filters are washed three times with the same buffer at 0–4° C. and their radioactivity is studied by means of a liquid scintillation spectrometer.

The specific binding is obtained by subtracting the binding determined in the presence of 1M of 8-OH-DPAT from the total binding. The characteristics of the binding are analysed by iterative analysis of the non-linear regression by computer, using the Ligand program [Munson and Rodbard, Anal. Biochem., 107, 220 (1980)].

The results for the compounds which are representative of the invention are given in Table 2 below.

TABLE 2

| Compound No. | Ki(nM) |
| --- | --- |
| 1 | 0.54 |
| 2 | 0.19 |
| 3 | 0.32 |
| 4 | 0.29 |
| 5 | 0.098 |
| 9 | 0.41 |
| 10 | 0.13 |
| 11 | 0.37 |
| 12 | 0.88 |
| 13 | 0.84 |

We claim:

1. The compounds corresponding to general formula I

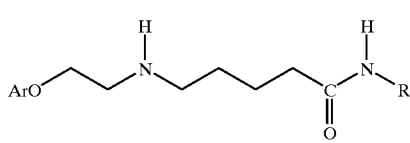

in which
Ar represents a phenyl substituted by one or more substituents;
R represents a hydrocarbon radical containing 1 to 10 carbon atoms chosen from linear or branched alkyl, or cycloalkyl radicals;
and salts of said products.

2. The compounds corresponding to general formula I as defined in claim 1, characterised in that the substituent(s) which the phenyl radical represented by Ar may bear are chosen from the lower alkoxy, —C(O)NR$_1$R$_2$, —NHC(O)R$_3$, —NH C(O)NR$_4$R$_5$, —NHC(O)OR$_6$ radicals in which R$_1$, R$_2$, R$_3$, R$_4$ and R$_5$ represent, independently, a hydrogen atom or a lower alkyl, and R$_6$ represents a lower alkyl.

3. The compounds corresponding to general formula I as defined in claim 1, characterised in that Ar represents a phenyl radical substituted by a substituent chosen from the methoxy, —C(O)NHMe, —NHC(O)Me, —NHCONH$_2$, —NHCONHMe, NHC(O)OMe radicals, and in the R represents the tert-butyl, neopentyl, cyclopentyl, cyclohexyl or cycloheptyl radical.

4. A compound of claim 1 selected from the group consisting of:
N-tert-5-[{2-(2-methoxyphenoxy)ethyl}amino]pentanamide;
N-cyclohexyl-5-[{2-(2-methoxyphenoxy)ethyl}amino]pentanamide;
N-neopentyl-5-[{2-(2-methoxyphenoxy)ethyl}amino]pentanamide;
N-cyclopentyl-5-[{2-(2-methoxyphenoxy)ethyl}amino]pentanamide;
N-cycloheptyl-5-[{2-(2-methoxyphenoxy)ethyl}amino]pentanamide;
N-cyclohexyl-5-[{2-(2-(methylaminocarbonyl)phenoxy)ethyl}amino]pentanamide;
N-neopentyl-5-[{2-(2-(methylaminocarbonyl)phenoxy)ethyl}amino]pentanamide;
N-neopentyl-5-[{2-(2-(aminocarbonylamino)phenoxy)ethyl}amino]pentanamide;
N-neopentyl-5-[{2-(3-(aminocarbonylamino)phenoxy)ethyl}amino]pentanamide;
N-cycloheptyl-5-[{2-(3-(aminocarbonylamino)phenoxy)ethyl}amino]pentanamide;
N-cyclohexyl-5-[{2-(3-(methylcarbonylamino)phenoxy)ethyl}amino]pentanamide;
N-neopentyl-5-[{2-(3-(methylcarbonylamino)phenoxy)ethyl}amino]pentanamide;
N-neopentyl-5-[{2-(3-(methoxycarbonylamino)phenoxy)ethyl}amino]pentanamide;
N-neopentyl-5-[{2-(3-(methylaminocarbonyl)phenoxy)ethyl}amino]pentanamide;
and the salts of said compounds with inorganic or organic acids.

5. A process for the preparation of products corresponding to general formula I as defined in claim 1, characterised in that
A) either a product corresponding to formula II

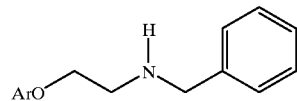

in which Ar has the meaning given in claim 1, is allowed to react with a product corresponding to formula III

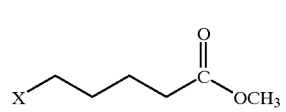

in which X represents a halogen or a pseudo halogen, in order to obtain a product corresponding to formula IV

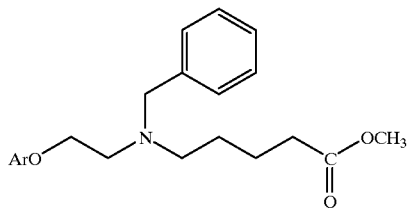

which product corresponding to formula IV is treated with an amine corresponding to the formula RNH$_2$ in which R has the meaning given in claim 1, in order to obtain a product corresponding to formula V

V

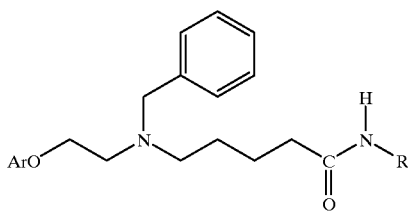

B) or a product corresponding to formula VI

VI

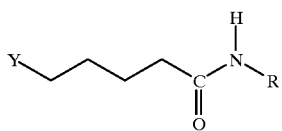

in which Y represents a halogen or pseudo halogen radical and R has the meaning given in claim 1 is allowed to react with N-benzylethanolamine corresponding to the formula

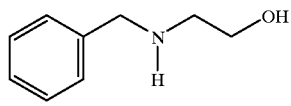

in order to obtain a product corresponding to formula VII

VII

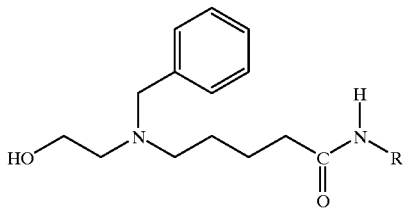

which is converted to a product corresponding to formula VIII

VIII

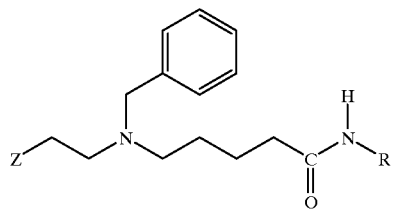

in which Z represents a halogen or pseudo halogen radical, which product corresponding to formula VIII is allowed to react with a compound corresponding to the general formula ArOH in which Ar has the meaning given in claim 1, in order to obtain a product corresponding to formula V as defined above, which product corresponding to formula V is converted to a product corresponding to formula I by cleavage of the benzyl function, and which product corresponding to formula I may be converted to acid salts by the action of the corresponding acid.

6. As medicaments, the products corresponding to formula I as defined in claim 1, and the additions salts with pharmaceutically acceptable inorganic or organic acids of the said products corresponding to formula I.

7. As medicaments, the products corresponding to formula I as defined in claim 2, and the addition salts with pharmaceutically acceptable inorganic or organic acids of the said products corresponding to formula I.

8. Pharmaceutical compositions containing, as active principle, at least one of the medicaments as defined in claim 6.

9. As new industrial products, the compounds of corresponding to formula IV, V, VII and VIII as defined in claim 5.

10. A method inhibiting gastric secretion in warm-blooded animals comprising administering to warm-blooded animals a gastric secretion inhibiting effective amount of a compound of claim 1.

11. A method of treating hypertension in warm-blooded animals comprising administering to warm-blooded animals a hypertensively effective amount of a compound of claim 1.

* * * * *